(12) United States Patent
Chan et al.

(10) Patent No.: US 7,066,968 B2
(45) Date of Patent: *Jun. 27, 2006

(54) EFFICIENT TWO-STEP METHOD OF COLORING AND LIGHTENING HAIR WITH LESS DAMAGE

(75) Inventors: Alexander C Chan, Cranbury, NJ (US); Stella Arcella, Oakland, NJ (US); John Brian Bartolone, Bridgeport, CT (US); Allan Robert Burger, Passaic, NJ (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 40 days.

This patent is subject to a terminal disclaimer.

(21) Appl. No.: 10/791,391

(22) Filed: Mar. 2, 2004

(65) Prior Publication Data

US 2005/0193501 A1    Sep. 8, 2005

(51) Int. Cl.
*A61K 7/13*    (2006.01)
(52) U.S. Cl. ............... 8/405; 8/406; 8/408; 8/410; 8/411; 8/412; 8/435; 8/585; 132/208; 424/70.1
(58) Field of Classification Search ............ 8/405, 8/406, 408, 410, 411, 412, 421, 435, 585; 132/208; 424/70.1
See application file for complete search history.

(56) References Cited

U.S. PATENT DOCUMENTS

| 5,603,734 | A | 2/1997 | Prota et al. ............... 8/424 |
| 5,980,586 | A | 11/1999 | Wenke et al. ............ 8/424 |
| 6,440,177 | B1 | 8/2002 | Orr ............................ 8/426 |
| 6,475,248 | B1 | 11/2002 | Ohashi et al. ............ 8/405 |
| 6,540,791 | B1 * | 4/2003 | Dias .......................... 8/111 |
| 6,596,035 | B1 | 7/2003 | Gutkowski et al. ....... 8/405 |
| 2003/0154562 | A1 * | 8/2003 | Sarojini et al. ........... 8/405 |
| 2003/0166182 | A1 | 9/2003 | Shao et al. |
| 2003/0188390 | A1 | 10/2003 | Matsunaga |

FOREIGN PATENT DOCUMENTS

WO    93/03706    3/1993

OTHER PUBLICATIONS

Co-pending and Co-owned Ser. No. 09/811,920, filed Mar. 19, 2001; Patel et al.
Co-pending and Co-owned Ser. No. 10/075,745, filed Feb. 14, 2002; Sarojini et al.
Co-pending and Co-owned Ser. No. 10/613,792, filed Jul. 3, 2003; Chan et al.
Co-pending and Co-owned Ser. No. 10/613,864, filed Jul. 3, 2003; Chan et al.

* cited by examiner

*Primary Examiner*—Eisa B. Elhilo
(74) *Attorney, Agent, or Firm*—Michael P. Aronson

(57) ABSTRACT

The present invention relates to a 2-step methods, and compositions for providing more vibrant, natural and long-lasting color to hair and at the same time reducing hair fiber damage associated with alternative current methods. In the first step the hair is contacted for a period of time with a dye precursor mixture containing specific oxidative hair dye precursors under conditions where these dyes are substantially inactive. Color is then developed in a second step by contacting the hair with a mixture of a peroxide compound and a persulfate salt. Surprisingly the 2-step method leads to considerable "lift" or lightening without negatively impacting the coloring ability of the oxidative dye. The invention also relates to kits providing the means to accomplish these steps.

16 Claims, No Drawings

EFFICIENT TWO-STEP METHOD OF COLORING AND LIGHTENING HAIR WITH LESS DAMAGE

FIELD OF INVENTION

The present invention relates to methods, and compositions for providing more vibrant, long-lasting color to hair and at the same time providing a more efficient and less damaging bleaching system to provide greater lift or lightening. The method includes two essential steps. First contacting the hair for a period of time with a dye precursor mixture containing specific primary intermediates and couplers under conditions where these dyes are substantially inactive. Color is then developed in a second step by contacting the hair with a mixture of a peroxide compound and a persulfate salt. The invention also relates to kits providing the means to accomplish these steps.

BACKGROUND OF INVENTION

Permanent hair colorants commonly come in two parts: a dye solution and a developer solution. In a conventional permanent hair coloring treatment, the dye solution and the developer solution are mixed and then immediately applied to the hair. After a time interval of about 25 to about 45 minutes, the hair is rinsed with water, treated with a post treatment conditioner, and then rinsed again with water.

The application of the dye solution and the developer solution affords permanent hair coloring. However, use of this conventional method does not provide maximum color deposition or retention and the range of color nuances especially in the red shades is limited.

The duration over which dyed hair remains colored is in principle only limited by the hair growth rate assuming the treatment does not affect the color of the hair as it is formed, i.e., the "roots". In practice dye films deposited on the hair are susceptible to extraction by repeated shampooing, erosion by combing and brushing, and fading by exposure to sunlight and oxygen. Red colors are particularly susceptible to these degrading processes and in an attempt to achieve sufficiently deep and long lasting red shades consumers often try to compensate by increasing the intensity of the initial color. However, this can lead to hair that has an unnatural or painted appearance.

The underlying problem in achieving vibrant and natural colors especially dark reds, that are also long-lasting and fade resistant, through oxidative dyeing of hair is that only a small portion of such colors enters the interior of the hair fiber during the dyeing process. As is well known, the color of oxidative dyes arises from the oxidative coupling of primary intermediates and secondary intermediate (often called couplers)—essentially dimerization and/or polymerization. Thus, oxidative coupling leads to an increase in molecular weight as well as an increase in conjugation. However, as the molecular weight rises, it becomes increasingly difficult for the polymerized dye to penetrate the hair fibers. Thus, the darkest colors are more likely to remain at the surface of the hair fibers where they are most susceptible to erosion, and abrasion. Being on the outside of the fibers these colors are also in an "optical environment" that is least similar to the environment of the natural melanins in hair, i.e., dispersed within the hair fiber matrix. The term "painted" often used to describe the unnatural appearance of darkly dyed hair is more than coincidental!

It has been shown in U.S. Patent Publication U.S. 2003, 0154,562 that a more long lasting and vibrant color is provided by a 2-step process in which oxidative dye precursors are applied to the hair in a substantially inactive form followed by the development of color with a composition that contains an oxidizing agent.

Although the 2-step process works well in terms of improved color retention and natural appearance it can require a relatively long contact time in the second developer step to achieve adequate lift or lightening when used on dark hair. The delivery of high lift is especially important to consumers with dark brown or black hair who desire to change the shade as well as the brightness of the hair. These consumers also have problems with conventional one-step process in terms of the fiber damage that is associated with strong bleaching systems.

A significant advantage of the present invention is that it provides a hair coloring method that not only will deliver long lasting, vibrant color but also deliver high lift or lightening especially on dark hair, coupled with a lower degree of fiber damage.

The following patents and publications have been considered:

U.S. Pat. No. 6,596,035 discloses a 1-step process for coloring the hair utilizing a combination of oxidative dyes a peroxide and a persulfate salt to simultaneously color and highlight the hair.

WO 93/03706 discloses a 1-step hair coloring composition including a coloring agent and a disaccharide that provides bleaching and coloring in a single step.

U.S. Pat. No. 6,440,177 discloses a 1-step process for coloring the hair utilizing water soluble basic azo dyes with a "category 2 bleach" which includes a persulfate salt. Oxidative dyes are stated to be unstable to such bleaching agents.

U.S. Pat. No. 5,980,586 discloses a 1-step process using a composition that includes an oxidative dye, a persulfate compound and an aminoethane thiol.

U.S. Patent Application Publication No. 2003/0188390 and U.S. Pat. No. 6,475,248 disclose specific direct dyes in combination with oxidizing agents in a 1-step hair coloring composition.

U.S. Patent Application Publication No. 2003/0166182 discloses a coloring system including a separately packaged thio compound, a mucuna plant extract, and an oxidizing agent.

U.S. Pat. No. 5,603,734 discloses a process for dyeing hair containing a cupric or ferrous salt, a catechol, and a persulfate oxidizing agent. The process is essentially carried out in one step.

None of the references cited above teaches that a sequential method for coloring the hair in which specific dyes in a predominantly non-anionic, and substantially oxidatively inactive form are first contacted with the hair followed by a developer lead to more vibrant colors and more varied tones.

SUMMARY OF THE INVENTION

It has now been found that the 2-step process can be improved further especially for coloring and changing the shade of dark hair by utilizing specific combinations of oxidizing agents in the second color development step that provide a greater "lift" or lightening effect.

Furthermore, it has been found that this higher lift can be delivered with this method while achieving a lower extent of hair fiber damage relative to currently practiced 1-step methods.

More specifically, the method involves carrying out the following sequential steps in the order indicated:

(a) contacting said hair with a substantially inactive mixture of oxidative hair dye precursors wherein the rate of oxidation of hair dye precursors devided by the rate of diffusion of hair dye precursors is less than about 1;

(b) allowing said mixture to remain in said hair for a period of about 5 minutes to about 60 minutes;

(c) contacting said hair with an aqueous developer composition containing a mixture of a persulfate salt, a peroxide, and a basifying compound, wherein the weight ratio of persulfate salt to peroxide is in the range from about 1 to about 4;

(d) allowing the composition in step (c) to remain on said hair for a period of about 30 seconds to about 60 minutes.

A second embodiment of the invention is a kit that allows individual consumers to conveniently practice the coloring method disclosed.

More specifically, the hair coloring kit includes:

(a) a hair colorant composition including oxidative hair dye precursors in a container, (b) a composition containing a peroxide in a container, (c) a composition containing a persulfate salt in a container, (d) written instructions that direct that the hair colorant composition is first applied to the hair as a substantially inactive mixture for about 5 minutes to about 60 minutes before a hair color developer composition created by mixing the peroxide composition with the persulfate salt composition is applied to the hair, wherein the oxidative hair dye precursors of the hair colorant composition satisfies the condition that the rate of oxidation of hair dye precursors divided by the rate of diffusion of hair dye precursors is less than about 1 when the hair colorant composition is applied to the hair before the hair is contacted with the hair color developer composition.

DETAILED DESCRIPTION OF THE INVENTION

As used herein wt % or simply % refers to the percentage of an ingredient in the composition based on the total weight of that composition. For example, when wt % or % is used to discuss the amount of an ingredient that is in the dye precursor mixture, e.g., an oxidative dye, this means percent by weight of that ingredient, in the this case the dye, as compared to the total weight of the dye precursor mixture. Similarly, when wt % or % is used to discuss a component of the developer mixture, it is the percent by weight of that ingredient compared to the total weight of the developer mixture.

Except in the operating and comparative examples, or where otherwise explicitly indicated, all numbers in this description indicating amounts or material or conditions of reaction, physical properties of materials and/or use are to be understood as modified by the word "about".

As used herein "inactive" or "substantially inactive" means that the oxidation hair dye precursors are not chemically reacting or are not chemically reacting to a substantial degree, so as to form coupled or polymerized hair color molecules, or it means that the oxidation hair dye precursors are not chemically reacting in a substantial manner so as to form coupled or polymerized hair color molecules.

Dye precursor mixtures refers generally to those compositions of the present invention which comprise oxidative hair dye precursors and are suitable for use on human hair, e.g., have the appropriate safety profile. Developer mixture refers generally to those compositions of the invention which are capable of inducing an oxidation reaction, a coupling reaction or a polymerization of the oxidative hair dye precursors that have been previously applied to the hair as part of the precursor mixture and are suitable for use on human hair. It should be understood that the latter step can be achieved by incorporating an active oxidizing agent in the developer mixture or by manipulating the pH or other chemical "environmental factor" to activate a nascent peroxide oxidizing agent that may already be present on the hair from contact with the precursor mixture.

The present invention relates to methods and compositions for achieving the permanent coloring of hair which methods involves two key steps performed in sequence:

1) contacting the hair with a substantially inactive dye precursor mixture for a period of about 30 seconds to about 60 minutes, followed by, 2) contacting said hair with an aqueous developer composition including a mixture of a persulfate salt, a peroxide, and a basifying compound, wherein the weight ratio of persulfate salt to peroxide is in the range from about 1 to about 4;

Without being bound by theory, it is believed that the above method provides the oxidation dye precursors with both the time and the chemical environment for diffusion into the hair shaft. The second step causes the formation of larger sized hair color molecules within the hair shaft. Because of their size, these hair color molecules have a lower tendency for diffusing out of the hair fibers. Because they are within the keratin matrix, they exhibit a more natural array of colors. The specific combination of peroxide and persulfate salt introduced following the methods disclosed herein provides sufficient oxidizing power to simultaneously lighten the hair but surprisingly does not destroy or render inactive the oxidative dye as described in the prior art.

The compositions and methods of the present invention may be used to color different types of hair such as Asian hair and Caucasian hair.

It will be understood by those skilled in the art that concentrations of oxidative hair dye precursors which may be employed in the present invention can be varied depending upon, for example, the hair type which is to be colored and on the coloring effect which is desired.

What follows is a description of the ingredients that can be included in the mixtures and the means for carrying out the steps of the present invention.

Dye Precursor Mixture

The dye precursor mixture of the present invention includes oxidative hair coloring precursors (also called oxidation dyes). Such oxidative hair coloring agents are used in combination with oxidizing systems, i.e., the developer, of the present invention to deliver color to the hair.

The dye precursor mixture also can contain ingredients used to enhance the solubility of the precursors in a predominantly aqueous medium ("solubility enhancers"). The mixture can also contain agents to control the pH so as to provide an optimal chemical environment for the precursors to interact with hair fibers ("pH control agents").

Oxidative Dyes

Permanent hair dye compositions as defined herein are compositions, which once applied to the hair, are substantially resistant to washout and abrasion.

The dye forming intermediates used in oxidative dyes can be aromatic diamines, naphthols, aminophenols, polyhydroxybenzenes, and their derivatives. These dye forming intermediates can be classified as; primary intermediates, and couplers (often also referred to as either secondary intermediates or modifiers). As used herein the term "precursor" means precursor, coupler, modifier, or intermediate and the like. Primary intermediates are chemical compounds, which by themselves will form a dye upon oxidation. The coupler or secondary intermediate is used with other intermediates for specific color effects or to stabilize the color.

At least two types of oxidative dyes are used in the invention: one type is a primary intermediate while the other type is a coupler.

Primary intermediates which are suitable for use in the compositions and processes herein include aromatic diamines, naphthols, polyhydric phenols, aminophenols and derivatives of these aromatic compounds (e.g., N-substituted and/or C-substituted derivatives of the amines, O-substituted and/or C-substituted derivatives of phenols).

Primary oxidation dye intermediates are generally colorless molecules prior to oxidation. Color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugation systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, and are capable of oxidative polymerization to yield higher molecular weight colored materials having extended conjugated electron systems.

Preferred primary intermediates and couplers have a pKa in the range from about 3 to about 10, preferably between about 5 and about 10. The term pKa has it usual chemical definition: the negative logarithm of the acid dissociation constant, i.e., $PK_a = -\log_{10} K_a$. Thus a pKa of 5 corresponds to an acid dissociation constant of $10^{-5}$.

In a preferred embodiment of the invention, the pH of the dye precursor mixture is adjusted such that less than 50%, preferably less than 25% and most preferably less than 10% of the molecules composing the dye precursors, i.e., the primary intermediate and coupler, are in their anionic form when in contact with the hair during the time period before the developer is applied. For example, if the precursor contains both an aniline and a phenol group, the pH should be below the pKa of the hydroxyl group of the alcohol. It has been found that this pH environment leads to a higher retention of dye precursor within the hair fiber and the high retention of color.

In an even more preferred embodiment of the invention, the pH of the dye precursor mixture is adjusted such that more than 50%, preferably more than 75% and most preferably more than 90%, of the molecules comprising the dye precursors, i.e., the primary intermediate and coupler, are in their neutral forms when in contact with the hair during the time period before the developer is applied. For example, if the precursor is a substituted aniline, the pH should be above the pKa of the conjugate acid of the aniline precursor. If the precursor contains both an aniline and a phenol group, the pH should be above the pKa of the conjugate acid of the amine but below the pKa of the hydroxyl group. It has been found that this pH environment leads to a still higher retention of dye precursor within the fiber and the highest retention of color.

Color modifiers (couplers), such as those detailed hereinafter, are preferably used in conjunction with the oxidation dye precursors herein and are thought to interpose themselves in the colored polymers during their formation and to cause shifts in the electronic absorption spectra thereof, thereby resulting in color changes. A representative list of oxidation dye precursors (primary intermediates and couplers) suitable for use herein is found in Sagarin, "Cosmetic Science and Technology"," Interscience, Special Edition, Volume 2, pages 308 to 310 which is herein incorporated by reference.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen, on the phenolic oxygen, or on the aromatic carbon, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes. Numerous examples of these and other synthetic and natural materials can be found in the compendium "Chemical and Physical Behaviour of Human Hair" 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre at chapter 45 by G. S. Kass (pp 841–920); 'Cosmetics: Science and Technology' 2nd Edn, Vol. 11 Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139). The above articles are hereby incorporated by reference.

Specific hair dyes which may be included in the compositions as the primary intermediate includes: 3-methyl-p-aminophenol; 2,3-dimethyl-p-aminophenol; p-phenylene diamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-di-(p-N,N-bis-(2-hydroxyethyl)-aminoanilino)-2-propanol; 2-methyl-4-dimethylaminoaniline; p-aminophenol; p-methylaminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2,5-diaminotoluene; 2-dimethylamino-5-aminopyridine; 2,4,5,6-tetra-aminopyrimidine; 4,5-diamino-1-methylpyrazole; 4,5-diamino-1-hydroxyethyl pyrazole, 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 5-chloro-2,3-dihydroxypyridine; 2-hydroxyethylamino-6-methoxy-3-aminopyridine; 3,4-methylenedioxyaniline; 7-hydroxyindole; 5-hydroxyindole; 2-bromo-4,5-methylenedioxyphenol; 3-amino-2-methylamino-6-methoxypyridine; 2-amino-3-hydroxypyridine; 4-hydroxy-2,5,6-triaminopyrimidine; 5-hydroxyindoline; 7-hydroxyindoline or combinations thereof.

Preferred primary intermediates for use in the invention include: p-phenylenediamine; p-aminophenol; N,N-bis(2-hydroxyethyl)-p-phenylenediamine; 2,5-toluenediamine; 2-methyl-p-aminophenol; 3-methyl-p-aminophenol; 2,3-dimethyl-p-aminophenol, p-methylaminophenol; 4,5,-diamino-1-hydroxyethyl pyrazole; 2,4,5,6-tetra-aminopyrimidine; 4-hydroxy-2,5,6-triaminopyrimidine; o-aminophenol; and mixtures thereof.

The most preferred primary intermediates are p-phenylenediamine, p-aminophenol; 3-methyl-p-aminophenol; N,N-bis(hydroxyethyl)-p-phenylenediamine, 2,5,-toluenediamine; o-aminophenol; and mixtures thereof.

The primary intermediate is generally present in the precursor mixture at a level from about 0.005 wt % to about 10 wt %, preferably from about 0.01 wt % to about 5 wt %, and most preferably from about 0.01 wt % to about 4 wt % based on the total weight of the dye precursor mixture.

The coupler (or secondary intermediate) is utilized to expand the color range by copolymerization with the primary intermediate. These materials can also accelerate color formation.

Specific hair dye intermediates that can be used as couplers in the present invention include: m-aminophenol; 2-methyl-1-naphthol; 1-acetoxy-2-methylnaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis (2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino)toluene; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 1-phenyl-3-methyl-5-pyrazolone; 5-hydroxy-1,4-benzodioxane; 2,6-dihydroxy-3,4-dimethylpyridine; 3,5-diamino-2,6-dimethoxypyridine; 2,6-bis-hydroxyethoxy-3,5-diaminopyridine; 3-amino-5-hydroxy-2,6-dimethoxypyridine; 4-hydroxyindole; 6-hydroxyindole; 2,6-diaminopyridine; 5-(3,5-diamino-2-pyridyloxy)-1,3-dihydroxypentane; 3-(3,5-diamino-2-pyridyloxy)-2-hydroxypropanol, 4-hydroxyindoline, 6-hydroxyindoline, and combinations thereof.

Preferred couplers for use in the invention include: resorcenol; m-aminophenol; 5-amino-2-methylphenol; 2-methyresorcinol, 1-naphthol; 2-methyl-1-naphthol; 2-(2,4-diamino-phenoxy)ethanol; 1-phenyl-3-methyl-5-pyrazolone; m-phenylenediamine; 4-hydroxyindole, 6-hydroxyindole; 4-chlororesorcinol; 2-chlororesorcinol, 2,6-diaminotoluene, 4-hydroxyindoline; 6-hydroxyindoline, 2,6-diaminopyridine, 2-methyl-5-hydroxyethylaminophenol, and mixtures thereof.

The most preferred couplers are o-aminophenol; 1-naphthol; 2-methylresorcinol; resorcinol; m-aminophenol; 5-amino-2-methylphenol; 2(2,4-diaminophenoxy)-ethanol; m-phenylenediamine; 1-phenyl-3-methyl-5-pyrazolone; 2,6,-diaminopyridine and mixtures thereof.

The coupler is generally present in the precursor mixture at a level from about 0.005 wt % to about 10 wt %, preferably from about 0.01 wt % to about 5 wt %, and most preferably from about 0.01 wt % to about 4 wt % based on the total weight of the dye precursor mixture.

The weight ratio of primary intermediate to coupler is generally in the range from about 100 to about 0.01, preferably from about 50 to about 0.05 and most preferably from about 10 to about 0.1.

It should be understood that the descriptions of primary intermediates and couplers given above is meant implicitly include the salt forms of those dye molecules that form stable salts. For example, the hydrochloride or sulfate salts in the case of amines, and the alkali metal salts in the case of phenols.

Solubility Enhancers

Water is the preferred principal solvent, carrier or diluent for the compositions according to the present invention. As such, the compositions according to the present invention may include one or more solubility enhancers as defined above. Generally, two preferred classes of solubility enhancers are solvents and surfactant systems.

Preferred solvents are miscible with water and innocuous to the skin. Solvents suitable for use herein include $C_1$–$C_{10}$ mono- or polyhydric alcohols and their ethers, glycerine, with monohydric and dihydric alcohols and their ethers. In these compounds, alcoholic residues containing 2 to 6 carbon atoms are preferred. Thus, a particularly preferred group includes ethanol, isopropanol, n-propanol, butanol, propylene glycol, ethylene glycol monoethyl ether, hexylene glycol and mixtures thereof.

The solvents may be present in the precursor mixture at a level of from about 0.1 to 20 wt %, preferably from about 0.1 wt % to about 15 wt % and most preferably from about 0.5 wt % to about 10 wt % based on the total weight of the precursor mixture.

The second class of solubility enhancer useful in the present invention is surfactants.

A particularly suitable class of surfactants is cationic surfactants. One type of preferred cationic surfactant is amine based and includes alkyl amines, alkylethoxy amines, ethoxylated alkyl amines and alkyl alkanol amines. Preferred alkyl groups have 1 to about 22 carbon atoms and can have a mixture of chainlengths, e.g, methyl and hexadecyl. The term amines include primary, secondary, tertiary and quaternary amines.

A second type of preferred cationic surfactant is amidoamines and includes C12–C22 alkyl or alkylethoxy mono, di and higher (poly)amidoamines which can be ethoxylated or unethoxylated. Examples include sodium dimethylaminopropyl coco-aspartamide, cocoamidopropyl dimethylamine, olivamidopropyl dimethylamine, soyamidopropyl dimethylamine, tallowamidopropyl dimethylamine, stearamidoethyl dimethylamine and mixtures thereof.

Another preferred class of surfactant that is suitable for use as a solubility enhancer is nonionic surfactants. This class includes long chain fatty alcohols, mono, di and triglyceride and their derivatives, long chain (C12–C18) alcohol ethoxylates and mixtures thereof. Examples include: steareth 20, oleth 10, laureth 4, PEG-12 glyceryl dioleate, glycerol stearate, sorbitan oleate, PPG-9 buteth-12 and mixtures thereof.

The level of surfactants used as solubility enhancers in the dye precursor mixture can generally range from 0.1 wt % to about 30 wt %, preferably from about 0.2 wt % to about 20 wt % and most preferably from about 0.25 wt % to about 15 wt % based on the total weight of the precursor mixture.

Both solvents and surfactants can and often are combined to achieve the desired state of solubility of the primary intermediate and coupler in the dye precursor mixture. However, it has been found that the type and level of solubility enhancer affect the ability of the oxidative dyes to absorb into the hair fibers and be retained after development. Although this can be difficult to predict, the optimum type and level of solubility enhancer can be determined empirically by treating a standard hair sample under controlled conditions with a precursor mixture and developing the color with an oxidizing agent. One such test protocol is the Piedmont In-Vitro Color Test and is described below. As discussed below, $\Delta E$ is the distance between two colors in the Tristimulus color space. Thus, $\Delta E$ is the change in color of the test hair sample after treatment with the precursor solution and development with a standard oxidizing agent. It has been found that the level and type of solubility enhancer used in the precursor solution should be such that this mixture provides a color change, $\Delta E$, of at least about 0.15 when measured by the in-vitro Piedmont Color Retention Test described below.

Nascent Oxidizing Agents

In a second embodiment of the invention a nascent peroxide oxidizing agent is incorporated in the precursor mixture that is applied to the hair in the first step. By nascent peroxide oxidizing agent is meant peroxide oxidizing agents that are potentially capable of initiating oxidative coupling and color reaction, but because of the chemical environment provided by the precursor solution, are rendered substantially inert.

An example of such a nascent oxidizing agent is hydrogen peroxide when present in a solution that has a pH less than about 4, preferably a pH between from about 2 to about 4. However, if a developer solution containing an alkaline buffering agent at a sufficient level is mixed with such a precursor solution the pH increases to a value greater than 7 where the hydrogen peroxide becomes active and initiates dye coupling and color formation.

When nascent peroxide oxidizers are used, it is preferred to adjust the precursor mixture to maintain the precursors not in their anionic forms (most preferably in their neutral forms) and substantially inert to oxidative coupling. This may require the incorporation of reversible oxidation inhibitors.

Developer Mixture

The developer mixture comprises ingredients capable initiating the chemical coupling or polymerization of the oxidative dye precursors which gives rise to the desired hair color. The hair color developer compositions of the invention may have a preferred pH in the range of from about 8.0 to about 11, more preferably from about 9.0 to about 10.5. To achieve this, the developer mixture also generally contains an alkaline pH control agent and may also contain other ingredients in an aqueous base.

Specifically the developer mixture when it is applied to the hair comprises an aqueous mixture of a peroxide oxidizing agent and a persulfate salt. The weight ratio of persulfate salt to peroxide should be in the range from about 0.75 to about 4, preferably from about 0.9 to about 3, and most preferably from about 0.9 to about 1.5.

Although the developer is applied to the hair as an aqueous mixture, the components can and usually are separate mixtures for stability reasons. These mixtures are mixed before use and some of the individual component mixtures may be solids. This is especially true of the persulfate salt component.

It is sometimes convenient to incorporate hair conditioning into the developer mixture or the separate packages that are mixed before use to generate the developer. This practice can avoid extra process steps and leave the hair manageable and having a desirable feel. However, when this is carried out it is critical to ensure that the conditioning agents are selected so as not to interfere with the oxidation step, for example, by not promoting wasteful decomposition. It is also necessary to select a conditioner that can function, i.e., adsorb on the hair, at the pH of the developer mixture on the hair.

Suitable active peroxide and persulfate salt oxidizing compounds and alkaline pH control agents are discussed below.

Peroxide Oxidizing Compounds

The peroxide oxidizing compounds or agents useful in the methods and compositions of the present invention are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide. These inorganic perhydrate salts may be incorporated as monohydrates, tetrahydrates etc. Also useful are melamine peroxide, sodium perborate, and sodium percarbonate. Mixtures of two or more of such inorganic peroxygen oxidizing agents can also be used. For all of these compounds, the active material is active hydrogen peroxide. One skilled in the art would recognize how much active hydrogen peroxide is desired in the hair coloring compositions that are being formulated and therefore one skilled in the art would be able to calculate how much of a peroxygen compound, such as for example, melamine peroxide, to employ.

The preferred peroxide oxidizing compound is hydrogen peroxide.

The levels of peroxide oxidizing agent used in the developer composition that is applied to the hair can be in the range from about 3 wt % to about 12 wt % preferably from about 5 wt % to about 10 wt %, and most preferably from about 6 wt % to about 8 wt % based on the total weight of developer.

Persulfate Salt

The persulfate salt is generally incorporated in powder bleach composition which generally contains a mixture of persulfate compounds which are capable of bleaching the hair, and other ingredients including particulate fillers, and, if desired, inorganic particulate colorants.

The powder bleach composition contains 15–65%, preferably 20–60%, more preferably 25–55% by weight of the powder bleach composition of at least one inorganic persulfate which may be ammonium persulfate, or an alkali metal or alkaline earth metal persulfate. Preferred are alkali metal or ammonium persulfates. Examples of alkali metal persulfates include lithium, sodium, potassium, cesium, and the like.

Particularly preferred are sodium and potassium persulfates. The persulfates are generally in particulate form, and have particle sizes ranging from about 0.1 to 200 microns.

Other components of the poweder bleach include the following.

Particulate Fillers: The remainder of the powder bleach composition comprises particulate fillers. Preferably, the powder bleach composition comprises 5–60%, preferably 8–55%, more preferably 10–50% by weight of the total composition of the particulate fillers. The term "particulate filler" means a generally inert particulate having a particle size of about 0.1–250 microns. The particulate fillers provide volume and, then mixed with the persulfates, dilute the persulfate particles. A variety of particulate fillers are suitable including inorganics, inorganic salts, hydrophilic colloids, carbohydrates, soaps, alkyl sulfates, and the like.

Examples of inorganics include silica, hydrated silica, alumina, attapulgite, bentonite, calcium oxide, chalk, diamond powder, diatomaceous earth, fuller's earth, hectorite, kaolin, mica, magnesium oxide, montmorillonite, pumice, talc, tin oxide, zeolite, zinc oxide, and the like.

Examples of suitable inorganic salts include aluminum, sodium, potassium, and magnesium salts of inorganic or organic acids. Examples of suitable salts include sodium metasilicate, sodium chloride, sodium silicate, aluminum citrate, calcium saccharin, calcium salicylate, calcium citrate, calcium benzoate, magnesium acetate, magnesium ascorbate, magnesium PCA, magnesium gluconate, potassium acetate, potassium benzoate, potassium citrate, potassium sorbate, sodium acetate, sodium ascorbate, sodium citrate, sodium gluconate, sodium pyruvate, and mixtures thereof.

Examples of suitable hydrophilic colloids include hydroxyethylcellulose, locust bean, maltodextrin, methylcellulose, agar, dextran, dextran sulfate, gelatin, pectin, potassium alginate, sodium carboxymethylchitin, xanthan gum, and the like.

Examples of suitable carbohydrates include sugars such as glucose, sucrose, maltose, xylose, trehelose, and derivatives thereof, in particular sugar esters of long chain, C 14–30 fatty acids, as well as dextrins, cellulosics, and derivatives thereof.

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

Inorganic Colorants: If desired, the powder bleach composition may comprise 0.01–2%, preferably 0.05–1%, more preferably about 0.1–1% of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

pH Control Agents

The dye precursor mixture and developer compositions of the present invention may have widely ranging pH values. When bases are present in compositions of the invention, the pH can range from about 7.0 to about 11.0, preferably 9 to 10.5. Acidic pH can range from about 3 to 7, preferably 5 to 7, and may be employed in those embodiments of the present invention wherein oxidation hair dye precursors are applied to the hair in admixture with nascent oxidizing compounds such as hydrogen peroxide. As already mentioned this is done because such low pH's will stabilize the hydrogen peroxide present and substantially suppress the color forming oxidation reaction.

pH adjustment can be effected by using well known acidifying agents or acidic buffering agents in the field of treating keratinous fibers, and in particular human hair. Such acidic pH control agents include inorganic and organic acids such as hydrochloric acid, tartaric acid, citric acid, and carboxylic or sulphonic acids such as ascorbic acid, acetic acid, adipic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Still other organic acids include maleic acid, malic acid, succinic acid, glycolic acid, glutaric acid, benzoic acid, malonic acid, salicylic acid, gluconic acid, polyacrylic acid, their salts, and mixtures thereof.

Especially preferred acidic pH control agents for use in the dye precursor and developer compositions include citric acid, lactic acid, glycolic acid, acetic acid, phosphoric acid and mixtures thereof.

Several different basic pH control agents can be used to adjust the pH of dye precursor and developer mixtures of the present invention (both in storage and at point of use). Nonlimiting examples of suitable basic buffering agents are ammonium hydroxide, urea, ethylamine, dipropylamine, triethylamine and alkylenediamines such as 1,3-diaminopropane, anhydrous alkaline alkanolamines such as, mono or di- or tri-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine aminoalkylpropanediol, and mixtures thereof.

Certain alkaline buffering agents such as ammonium hydroxide and monoethanolamine (MEA), urea and the like, can also act as hair swelling agents (HSA's).

Preferred alkaline or basic pH control agents for the dye precursor and developer compositions according to the present invention, is ammonium hydroxide, monoethanolamine, and/or sodium hydroxide.

The level of pH control agent used in either the dye precursor or developer mixture can generally range from a value of about 0.2 wt % to about 20 wt %, preferably from about 0.5 wt % to about 18 wt % and most preferably from 1 wt % to about 15 wt % based on the total weight of the developer mixture that is applied to the hair.

In hair coloring kits of the invention which contain the hair colorant compositions, i.e., the oxidation dye precursors, of the present invention and the hair color developer compositions of the present invention, a portion of the oxidizing agents, may be present in either solid or liquid form or a combination thereof. For example, hydrogen peroxide, in an acid buffering agent solution, to stabilize the hydrogen peroxide, and a mixture in solid powder form that contains the persulfate salt. Phosphoric acid is a preferred agent for buffering hydrogen peroxide solutions.

Thickeners

Thickeners may be optionally included in the oxidation hair colorant compositions and hair developer compositions of the invention, and specifically thickeners may be included in the hair dye precursor part and the hair color developer parts of the invention. Long chain fatty alcohols having from about 11 to about 22 carbon atoms in the long fatty chain can be thickener constituents of the compositions of this invention. These alcohols can be used alone, or in admixture with each other. When included in the compositions, the alcohol is preferably present at from about 0.5 to about 10 weight percent of the composition, and more preferably at from about 2 to about 8 weight percent.

Lauryl alcohol, oleyl alcohol, myristyl alcohol, stearyl alcohol, behenyl alcohol and the like, and mixtures thereof are contemplated herein as thickeners. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as CARBOPOL, ACULYN 28, STRUCTURE 2001, 3001, and XL, and ACROSYL and mixtures thereof. Preferred thickeners for use herein are ACULYN 22 (RTM), steareth-20 methacrylate copolymer; ACULYN 44 (RTM) polyurethane resin and ACUSOL 830 (RTM), acrylates copolymer that are available from Rohm and Haas, Philadelphia, Pa., USA. Additional thickening agents suitable for use herein include sodium alginate or gum arabic, or cellulose derivatives, such as methylcellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Other Optional Ingredients

The dye precursor compositions and developer compositions of the present invention can comprise a wide range of optional ingredients. Examples of these functional classes include: mildness enhancers such as cholesterol and its derivatives, hair swelling agents, anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous), and hair fiber lubricants. Examples of other functional classes of materials useful in the art include solubilizing agents, sequestrants, amino acids, ingredients that impart shine, hydrolysed proteins and the like.

It may also be advantageous to include agents that condition the hair to improve combability and impart a silky/moisturized feel to the hair after it dries. Such agents include fatty long chain amines and their derivatives, silicones such as dimethicone and amodimethicone, long chain fatty acohols and mixtures of these materials. Such conditioners can be incorporated in either the precursor mixture, the developer mixture Conditioners can also be packaged separately when kits are employed.

Other Optional Steps

Aligning Means

"Aligning and distributing means of the invention" is used interchangeably with "aligning and distributing means" or simply "aligning means" and refers to a means or implement employed to align the hair and distribute the dye precursor after the dye precursor is applied to the hair but before the hair is contacted with the developer mixture.

An optional step that can be incorporated in the process is the application of means for aligning the hair after it has been in contact with the precursor mixture for a period of time but before the developer is applied.

A variety of implements can serve as an aligning means in the invention. These includes combs and picks, brushes, sponges, towlettes, and various modifications and combinations of these basic elements that are known in the art.

Alignment means that have at least one comb or one brush element are especially preferred. The comb is an implement of grooming dating from ancient times yet patents on various improvements continue to appear. As used here a comb element consists of strip of material (e.g., plastic) to which are fixed one or more rows of teeth. The comb element can be of simple construction or it can be contoured or have features that induce highlighting, for example, variable spacing or length of the teeth or wells cut into the fixing strip.

Optionally, the comb element can also incorporate absorbent features that additionally remove excess dye or a portion of excess dye precursor solution that has not penetrated the hair. Such "drying combs" are well known in the art. For example, U.S. Pat. No. 4,013,086, incorporated by reference herein, discloses a combing device that accommodates disposable absorbent sheet sandwiched between its split teeth. An alternative means for incorporating an absorbent material is disclosed in U.S. Pat. No. 1,166,361, incorporated by reference herein. Wingard in U.S. Pat. No. 4,421,129 incorporated by reference herein, and the references incorporated therein describes still other combination aligning and drying combs.

A brush element as defined herein is an aligning means that has bristles set into a handle. The handle can be rigid or flexible. The bristles can be single rigid filaments or tines, flexible fibers, or tufts of fibers. The bristles can be of uniform length or they can be of different lengths either to allow the brush element to promote highlighting effects by opening channels or different depths or to allow the brush to be contoured to conform to the shape of the head. The brush can also incorporate step features which further promote highlighting, such as is disclosed in U.S. Pat. No. 6,453,909 B1, incorporated by reference herein. Further, the bristles can be distributed in rows in a planar configuration or radially distributed to form an arc.

Preferred brush elements are comprised of a planar plastic base to which rows of rigid plastic tines are affixed as these are simple and inexpensive to manufacture.

The brush element can also incorporate an absorbent feature that performs the secondary function of removing excess dye precursor solution that has not penetrated the hair fibers. For example, the brush can incorporate a hydrophilic foam pad, or other absorbent material such as a nonwoven sheet. U.S. Pat. No. 4,856,541, and U.S. Pat. No. 5,002,075, both incorporated by reference herein, describes brushes that incorporate a hydrophilic polyurethane foam affixed on the handle at the base of the tines.

Both the comb and brush elements can be constructed of materials that can also assist in the absorption of excess dye precursor solution. Examples of absorptive plastic materials of construction that are known to aid drying are disclosed in U.S. Pat. Nos. 3,992,336, 4,018,729, and 4,421,129, all incorporated by reference herein.

Towelettes, and clothes, are still other types of implements that can serve as aligning means especially in markets where low cost is an important issue. These can be of woven or non-woven construction, and be planar or contoured to fit the fingers or hand (e.g., in the form of gloves). Such implements can also incorporate textured surfaces that promote alignment of the hair fibers.

Sponges or foams can also serve as an aligning implement and additionally incorporate a handle element. These implements can range from planer sheets to various contour shaped articles and comprise small cells or large open cells with diamond shaped faces.

A still further type of implement can be of the type described in U.S. Pat. No. 6,138,376, incorporated by reference herein, for the passive drying of hair. This device consists of two elongated elements coupled in a open/close relationship (analogous to a closes—pin) which can used to align the hair. Again this element can incorporate an absorbent element that removes excess dye precursor while performing the primary function of aligning the hair.

The aligning means can also comprise a combination to the above-described elements. Combinations of brush and comb elements are well known in the art and an early example may be found in U.S. Pat. No. 660,893.

The aligning means described above can also incorporate a means for dispensing either the dye precursor mixture, the developer or both so as to achieve a simple to use system. Examples of potential systems are provided in U.S. Pat. Nos. 6,505,983 B1, 5,975,089, 5,024,243, and 6,260,557 all incorporated by reference herein.

Regardless of whether the aligning means is a separate implement or part of an integrated system, it is applied to the hair between the application of the dye precursor mixture and the application of the developer, i.e., after the hair is contacted with the dye precursor (including any nascent peroxide oxidizing agent when desired) but before the hair is contacted with the developer. The time interval between contacting the hair with dye precursor and alignment of the hair is generally between 30 seconds to about 60 minutes, preferably 5 minutes to 45 minutes and most preferably between 10 minutes and 30 minutes.

Application of Methods and Compositions of the Invention

The dye precursor and hair color developer parts of the present invention are applied sequentially to the hair. Optionally, a means is applied to the hair for aligning the hair fibers and distributing the precursor mixture, i.e., after the hair is contacted with the dye precursor part. A period of about 30 seconds to about 60 minutes, preferably about 5 minutes to about 45 minutes, and most preferably from about 15 minute to about 25 minutes, is allowed to elapse after which the alignment means is applied to the hair. In this case, the developer is typically applied 0.5 to 20 minutes after the hair alignment step. The alignment and distributing means can be a comb, a brush, a disposable towellette, and a sponge like device (large or small cells) or a device that comprises a combination of these elements or in further combination with a dispensing means as described above. The consumer can supply the alignment and distributing means or it can be a specialized tool provided as part of the kit alone.

In any case, after the developer is applied it is allowed to remain in contact with the hair for about 1 minute to about 60 minutes, preferably for about 5 minutes to about 45 minutes, and most preferably from about 15 minute to about 30 minutes, The process described above is in sharp contrast to conventional permanent hair coloring methods which require that the hair be contacted with a dye precursor composition and a hair color developer composition, simultaneously or nearly simultaneously. Without being bound by theory, it is believed that an advantage of the methods of the present invention is that smaller hair dye precursor molecules are given time to diffuse into the hair shaft. Then when the hair is contacted with the hair color developer part, the smaller hair dye precursor molecules that are within the hair shaft undergo coupling and polymerization reactions so as to form larger color molecules that are trapped within the hair shaft because of their size. Another advantage of the methods of the present invention as compared to conventional permanent hair coloring methods, is that conventional permanent hair coloring methods cause much of the coupling and polymerization of the hair dye precursors to occur outside of the interior of the hair shaft and are wasted. Large hair color molecules are formed, and because of their size, these large hair color molecules cannot diffuse into the hair shaft.

The above physical phenomena can be described by the following chemical equations. When $$R_o/R_d \geq 1$$

where $R_o$ is the rate of oxidation of hair dye precursors and $R_d$ is the rate of diffusion of hair dye precursors, diffusion of hair color precursor into the hair fibers is limited by the rapid formation of dye molecules outside the hair fiber. When rate of oxidation of hair dye precursors divided by the rate of diffusion of hair dye precursors is greater than or equal to about 1, diffusion of dye precursors into the hair fiber is limited due to their rapid oxidation outside the hair fiber. In this case, the rate of oxidation is much higher or equal to rate of diffusion that the small precursor molecules undergo oxidation before they get a chance to penetrate inside the hair fiber. Since oxidation leads to formation of bigger color molecules, they cannot diffuse into the hair fiber as the small precursor molecules resulting in surface deposition of colored molecules. Thus, for color retention in hair, the color molecules should be formed inside the fiber and not on the surface.

In contrast when $$R_o/R_d<1$$

diffusion of hair color precursor becomes rate limiting and the dye precursors are able to penetrate the fibers to a greater extent. When rate of oxidation of hair dye precursors divided by the rate of diffusion of hair dye precursors is less than or equal to about 1, the oxidation rate is much lower than or equal to diffusion rate thereby increasing the diffusion of precursor molecules into the hair fiber. Ideally, competing oxidation reactions should be eliminated to maximize diffusion of color precursors inside the hair fiber. In a conventional one step process this is impossible since the dye precursors are mixed with the oxidant prior to application resulting in oxidation immediately after mixing.

The step 1 of the 2-step coloring process is designed to maximize the diffusion process through minimizing oxidation reactions by excluding the oxidant. Thus in step 1, the rate of oxidation divided by the rate of diffusion is less than or equal to about 1.

The above model helps to explain the higher retention of color when oxidative hair dyes are used in combination with a persulfate/peroxide oxidation system in a 2-step process compared with prior art attempts using a 1-step process. In the case of a 1-step process the more potent oxidizing system rapidly produces oligomers and polymers which are simply two big to diffuse into the hair fiber in a reasonable time period. In contrast in a 2-step process the reactive primary intermediates and couplers have already diffused into the hair fibers. Here rapid oxidation is no longer an issue since the intermediates are already in the fibers, i.e., diffusion of dye is no longer rate determining in the pressence of the oxidizing system.

Evaluation Methodology

Assessment of Initial Color and Color Change

The equipment used to measure both the initial color and color change on substrates (hair/skin) dyed with the singly packaged low pH coloring compositions of the present invention is a Hunter spectrophotometer. The value used to express the degree of color change induced by the combined treatment of precursor mixture and developer on any particular hair substrate is $\Delta E$. The term $\Delta E$, as defined herein, represents the distance in Tristimulus color space between two different samples, e.g., before and after treatment. $\Delta E$ is computed from the measured changes of the Tristimulus vales $\Delta L$, $\Delta a$, and $\Delta b$ values by:

$\Delta E$=difference of color of treated and non-dyed hair:
$\Delta E=\sqrt{(\Delta L^2+\Delta a^2+\Delta b^2)}$ where L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b' is a measure of the yellow and blue quotients (color hues) such that positive equates to yellow and negative equates to blue. $\Delta L$ is also a useful measure of the effectiveness of the hair coloring system in delivering "lift" or lightening benefits to the hair.

Piedmont In-vitro Color Retention Test

A 1 gm tress Piedmont hair from International Hair Products Inc. is first treated with the aqueous dye precursor composition at a level of between 1.5 to 3 gm precursor mixture per gm of hair. The precursor was distributed over the hair surface by means of a styling brush of the type commonly employed by salon stylists. After 20 minutes from the completion of the application of the precursor composition an aqueous developer solution (typically 1.5 gm to 3. gm per gm of hair) is then applied to the hair by means of a styling brush to develop the color. The hair tresses are dried overnight and the values of L, a, and b, are then measured and the change in color index, $\Delta E$, of the tress compared to their initial value is then computed from the above equation.

It has been found that the color change produced by oxidative dyes can depend on the chemical environment provided by the precursor mixture when it comes into contact with the hair. Precursor mixtures useful in the present invention should at least be capable of producing a color change, $\Delta E$, of at least 0.15 units when used in the above test procedure.

When appropriate the above method can be modified to include an aligning and distributing step interspersed between the application of the precursor and the application of the developer.

The resistance of the treatment to fading by for example shampoo treatment can also be measured in a similar way. After the above dye treatments, the dried hair tresses are placed in a tube containing a 10% shampoo solution and agitated for 1 hour by means of a mechanical shaker. The tresses are then rinsed and dried. The values of L, a, and b, are then measured and the change in color index, $\Delta E$, is computed and compared to their value before shampoo extraction or to the initial untreated hair as desired.

In-vitro Measurement of Wet Tensile Strength

The tensile properties of hair was measured by an in-vitro technique using a Diastron, Ltd., fully automated tensile tester Model MTT 670. The two parameters employed to asses the effect of treatment on mechanical properties ogf the hair is the elastic modulus and the break force (the tensile force just required to break the hair).

Prior to testing, fiber diameters were assessed using a commercially available Mitutoyo Laser Scan Micrometer. Single hair fiber test were carried out on hair presoaked in water for 30 min. During the test the fiber (gauge length of 30 mm) was stretched at an extension rate of 20 mm/min and the load versus extension curves were recorded. An average of 35 hairs were used for each sample.

The slope of the linear portion of the tensile curve is defined as the elastic modulus $[N/m^2]$, was evaluated. The force at which the individual hair fibers break, designated the break load $[N/m^2]$, is also determined automatically by the instrument and was recorded.

EXAMPLES

The following examples are shown as illustrations only and are not intended to limit the scope of the invention.

Example 1

Illustration of Superiority of Two-Step Method of the Invention Compared With Other Methods Utilizing Oxidative Dyes, Peroxide and Persulfate Salts The oxidative hair dye precursor mixture, the peroxide compositions and the persulfate salt composition utilized for Example 1 and comparative examples C1A and C1B are given in Table 1 A–C.

For example Ex 1A, a 5 gm tress of piedmont hair was treated with 10 gm of the oxidative hair dye precursor mixture (Table 1 A) for 20 minutes according to the procedures outlined under Evaluation Methodology. Without rinsing, the hair was then transferred to a developer solution that was formed by combining 10 gm of the peroxide solution of Table 1B with 1.58 gm of the persulfate "powder" of Table 1C. After an additional 25 minutes the tress was rinsed with distilled water and air dried.

For comparative example C1A the treatment method disclosed in U.S. Pat. No. 6,596,035 was employed. Here, a 5 gm hair tress was soaked in a mixture formed by the direct combination of 10 gm of oxidative hair dye precursor mixture of Table 1A, 10 gm of aqueous peroxide compoistion of Table 1B, and 1.58 gm of the solid sodium persulfate mixture of Table 1C. After 45 minutes the tress was rinsed and dried.

For comparative example C1B, a 5 gm hair tress was soaked for 20 minutes in mixture formed by combining the dye composition of Table 1A with the persulfate salt composition of Table 1C. The tress was then soaked an additional 25 minutes in 10 gm of the peroxide solution of Table 1B, rinsed with water and dried.

After drying, Tristimulus color indices of the three tresses were measured and the color difference calculated as set forth in the EVALUATION METHODOLOGY section above. A comparison of the color changes produced by the three treatment methods described above is given in Table 1D.

The results in Table 1D demonstrates that the color change provided by the sequential 2-step process described herein (Ex 1) is much greater (over 5 fold improvement) than the color change produced by the 1-step method described in the prior art (C1A). An alternative 2-step method where the hair is treated in a combination of persulfate salt and oxidative dye and then treated with peroxide also produced an inferior result (one half the color change provided by the 2-step method set forth herein).

TABLE 1A

Oxidative hair dye precursor mixture

| INGREDIENTS | WT % |
|---|---|
| Hydroxypropyl starch phosphate ester | 2 |
| Propylene glycol | 1.5 |
| Citric acid | 0.1 |
| Stearamidopropyl dimethylamine | 0.5 |
| Dicetyldimonium chloride | 2.1 |
| Stearyl alcohol | 0.45 |
| Ceteareth-20 | 1.05 |
| Cetyl alcohol | 3.6 |
| Potassium chloride | 0.1 |

TABLE 1A-continued

Oxidative hair dye precursor mixture

| INGREDIENTS | WT % |
|---|---|
| EDTA 4Na | 0.1 |
| Na sulfite | 0.2 |
| p-Phenylenediamine | 0.08 |
| 3-Methyl-p-aminophenol | 0.15 |
| p-Aminophenol | 0.2 |
| 4-Amino-2-hydroxytoluene | 0.2 |
| 5-(2-Hydroxyethyl)amino-2-hydroxytoluene | 0.15 |
| Resorcinol | 0.5 |
| Dimethicone fluid | 0.1 |
| Cyclopentasiloxane | 1.8 |
| D. I. water | to 100 |

TABLE 1B

Aqueous peroxide composition

| INGREDIENTS | WT % |
|---|---|
| Citric acid | 0.03 |
| Stearamidopropyl dimethylamine | 0.5 |
| Dicetyldimonium chloride | 2.7 |
| Stearyl alcohol | 0.25 |
| Ceteareth-20 | 0.58 |
| Cetyl alcohol | 1.6 |
| Propylene glycol | 2.67 |
| EDTA 4Na | 0.13 |
| Potassium chloride | 0.07 |
| Phosphoric acid | 0.07 |
| Dimethicone fluid | 0.1 |
| Cyclopentasiloxane | 1.8 |
| Hydrogen peroxide (50%) | 8.0 |
| Water | to 100 |

TABLE 1C

Persulfate salt composition

| INGREDIENTS | WT % |
|---|---|
| Sodium persulfate | 50 |
| Fillers and flow permoters | 35 |
| Thickeners, wetting agents and other inert ingredients | to 100% |

TABLE 1D

Comparison of color changes produced by different coloring methods used in Example 1

| Sample | Treatment method | ΔE (versus control) | L* | a* | b* |
|---|---|---|---|---|---|
| Control | Untreated | 0 | 70.48 | 2.27 | 21.59 |
| Ex 1 | 2-Step of invention<br>1. Oxidative dye alone<br>2. Mixture of peroxide and persulfate | 37.44 | 36.12 | 17.14 | 21.55 |
| C1A comparative example | 1-Step as in U.S. Pat. No. 6,596,035<br>Mixture of oxidative dye, persulfate and peroxide | 7.24 | 68.11 | 8.45 | 24.54 |

TABLE 1D-continued

Comparison of color changes produced by different coloring methods used in Example 1

| Sample | Treatment method | ΔE (versus control) | L* | a* | b* |
|---|---|---|---|---|---|
| C1B comparative example | Alternative 2-step<br>1. Mixture of oxidative dye and persulfate<br>2. Peroxide composition | 18.56 | 53.56 | 9.97 | 21.55 |

Example 2

Hair Lightening ("Lift") and Fibre Damage

This example illustrates the excellent lightening ability ("Lift") of the instant method and its superior ability to induce less damage than other bleaching methods. To measure the separately measure the lightening (bleaching) component in the instant 2-step process a "placebo" for the oxidative hair dye precursor compoistion was employed. This composition was similar to that used in Example 1 (Table 1A) but did not contain and oxidative dyes. It is set forth in Table 2A.

A light brown hair tress was first treated with the "placebo" composition (Table 2A Ex 2) for 20 minutes according to the procedures outlined under Evaluation Methodology. Without rinsing, the hair was then transferred to a developer solution that was formed by combining 10 gm of the peroxide solution of Table 1B with 1.58 gm of the persulfate "powder" of Table 1C. After an additional 25 minutes, the tress was rinsed with distilled water and air dried. The process was repeated 4 times.

A second brown hair tress was treated for 45 min in a commercial peroxide 1-step bleaching system sold L'Oreal under the name PREFERENCE LB03 (comparative example C2A). The tress was rinsed and as above and the process repeated 4 times.

A third brown hair tress was treated for 45 min in a second commercial 1-step bleaching system sold by L'Oreal under the name FERIA BLEACH BLONDING 200. This bleaching system utilizes a persulfate salt booster. The tress was rinsed and as above and the process repeated 4 times (Comparative example C2B).

The cumulative lightening (ΔL—-value), color change (ΔE), and % change in elastic modulus and breaking strength are recorded in Table 2B.

It is seen from the results in Table 2B that the instant method provides excellent lift (lightening as seen either from the increase in L value or the change in color index) and provides the least damaging (smallest change in elastic modulus and break strength) Vs the comparative treatments tested.

TABLE 2A

Oxidative hair dye precursor mixture used in Example Ex 2

| INGREDIENTS | WT % |
|---|---|
| Hydroxypropyl starch phosphate ester | 3.0 |
| Propylene glycol | 0.5 |
| Citric acid | 0.1 |
| Stearamidopropyl dimethylamine | 0.5 |
| Dicetyldimonium chloride | 2.1 |
| Stearyl alcohol | 1.1 |
| Ceteareth-20 | 0.4 |
| Cetyl alcohol | 3.6 |
| Potassium chloride | 0.1 |
| EDTA 4Na | 0.1 |
| Na sulfite | 0.15 |
| Dimethicone fluid | 0.1 |
| Cyclopentasiloxane | 1.8 |
| D. I. water q.s. | to 100 |

TABLE 2B

Hair lightening results for Example 2

| | | Cumulative lightening (4 treatments) | | | | |
|---|---|---|---|---|---|---|
| | Treatment | ΔE | ΔL | L | a* | b* |
| Control | Untreated hair | 0 | 0 | 15.7 | 3.16 | 22.5 |
| Ex 2<br>Current invention | 2-step method<br>1. Placebo Table 2A; 20 min<br>2. Peroxide/persulfate mixture (Table 1B/C); 25 min | 33.7 | 32.6 | 48.3 | 10.2 | 27.4 |
| C2A<br>L'Oreal LB03 | 1-Step (peroxide)<br>L'Oreal PREFERENCE LB03; 45 min | 23.7 | 22.8 | 38.5 | 9.5 | 21.9 |
| C2B<br>Feria 200 | 1-Step (peroxide/persulfate<br>l'Oreal FERIA 200; 45 min | 48.3 | 47.5 | 63.2 | 8.4 | 29.6 |

TABLE 2C

Effect of treatments on mechanical properties of hair for Example 2

| | Treatment | Effects of Cumulative treatment (4×) on mechanical properties | | | |
|---|---|---|---|---|---|
| | | Elastic modulus N/m² | Break load N/m² | % Change in Modulus | % Change in break strength |
| Control | Untreated hair | 1.52 E09 | 1.90 E08 | 0 | 0 |
| Ex 2 Current invention | 2-step method 3. Placebo Table 2A; 20 min 4. Peroxide/persulfate mixture (Table 1B/C); 25 min | 1.43 E09 | 1.83 E08 | −13.7 | −3.6 |
| C2A L'Oreal LB03 | 1-Step (peroxide) L'Oreal PREFERENCE LB03; 45 min | 1.20 E09 | 1.65 E08 | −21.1 | −13.1 |
| C2B Feria 200 | 1-Step (peroxide/persulfate l'Oreal FERIA 200; 45 min | 1.19 E09 | 1.58 E08 | −21.7 | −16.8 |

Example 3

Color Change Produced by the 2-Step Peroxide/Persulfate Method Compared With Conventional 1-Step Peroxide Based Oxidative Dye Systems A swatch of gray hair (Ex 3) was first treated for 20 minutes with the oxidative hair dye precursor mixture whose composition is set forth in Table 3A. This treatment was followed by a 25 minute treatment in a composition prepared by mixing 10.0 gm of the peroxide composition set forth in Table 3C and 1.58 gm of the persulfate powder composition set forth in Table 3C.

A second gray hair tress (Comparative example C3) was treated for 45 minutes in a mixture of 10 gm of a commercial high lift product sold by L'Oreal, PREFERENCE LB02, to which was added the same oxidation dye precursors as used for the first gray hair tress. The concentration of the dye precursors in the LB02 composition is the same as that given in Table 3A.

The coloring results are shown in Table 3D and clearly demonstrate that the 2-step persulfate/peroxide bleach system provides a more intense coloration to the gray hair as seen from the larger decrease in L value (smaller the L value the darker the color).

TABLE 3A

Oxidative hair dye precursor mixture used in Ex 3

| INGREDIENTS | WT % |
|---|---|
| Hydroxypropyl starch phosphate ester | 3 |
| Propylene glycol | 0.5 |
| Citric acid | 0.1 |
| Stearamidopropyl dimethylamine | 0.5 |
| Dicetyldimonium chloride | 2.1 |
| Stearyl alcohol | 1.1 |
| Ceteareth-20 | 0.4 |
| Cetyl alcohol | 3.6 |
| Potassium chloride | 0.1 |
| EDTA 4Na | 0.1 |
| Na sulfite | 0.15 |
| p-Aminophenol | 0.2 |
| 5-Amino-o-cresol | 0.22 |
| Dimethicone fluid | 0.1 |
| Cyclopentasiloxane | 1.8 |
| D. I. water | to 100 |

TABLE 3B

Aqueous peroxide composition used in Ex 3

| INGREDIENTS | WT % |
|---|---|
| Citric acid | 0.06 |
| Stearamidopropyl dimethylamine | 0.5 |
| Dicetyldimonium chloride | 3.0 |
| Stearyl alcohol | 0.58 |
| Ceteareth-20 | 0.25 |
| Cetyl alcohol | 1.6 |
| Oleth-10 | 0.7 |
| Propylene glycol | 2.7 |
| EDTA 4Na | 0.13 |
| Potassium chloride | 0.07 |
| Phosphoric acid | 0.07 |
| Ammonium chloride (20%) | 1.9 |
| Ammonium hydroxide (28%) | 11.0 |
| Dimethicone fluid | 0.1 |
| Cyclopentasiloxane | 1.8 |
| Hydrogen peroxide (50%) | 8.0 |
| Water | to 100 |

TABLE 3C

Persulfate salt composition used in Ex 3

| INGREDIENTS | WT % |
|---|---|
| Sodium persulfate | 50 |
| Fillers and flow promoters | 35 |
| Thickeners, wetting agents and other inert ingredients | to 100% |

TABLE 3D

Hair color results for Example 3

| Treatment | Treatment | ΔL | L | a* | b* |
|---|---|---|---|---|---|
| Control | Untreated hair | 0 | 34.54 | 1.63 | 8.17 |
| Ex 3 | 2-step method | 2.24 | 32.3 | 14.2 | 17.9 |
| This invention | 1 dye composition of Table 3A 20 min<br>2 Peroxide/persulfate mixture<br>(Table 3B/3C); 25 min | | | | |
| L'Oreal product | 1-Step (peroxide)<br>Mixture of Composition Table 3A<br>and L'Oreal PREFERENCE LB03; 45 min | 0.76 | 35.3 | 16.8 | 18.4 |

Example 4

This Example Illustrates a Kit Comprising an Additional Instruction Sheet The invention also relates to a kit for carrying out the hair coloring method of the invention. The kit may comprise a hair dye precursor part, an optional alignment and distributing means, a color developer comprising a hydrogen peroxide solution and an alkaline pH control solution (e.g., an alkaline buffer solution), a persulfate salt composition in the form of a powder, and a post treatment solution. Each component may be in a separate container or in a dual container, as described herein. The kit may optionally comprise an integrated system that incorporates two or more of the above means to carry out the above step, e.g., an aligning means and a developer. However, it is preferred to carry out alignment, e.g., combing, is a separate step.

The kit also contains written instructions that explain how the compositions of the invention are used. For Example, "Apply dye precursor mixture to hair. After 10 to 25 minutes, add the persulfate powder to the peroxide solution and mix well to dissolve. To this mixture next add the alkaline component to activate the developer and lifting action and then apply the mixture to the hair".

The consumer can admix the components of the kit according to written instructions, to obtain the aqueous reaction mixture. After treatment for a desired time with the hair dye precursor composition, the implement of the kit is used to align the hair and distribute the dye, followed by application of the developer. The mixture of hair developer and hair dye may be removed, preferably with water or a conventional shampoo or a conventional conditioning shampoo.

Alternatively, and with respect to an embodiment of the invention wherein hair dye precursors are in admixture with the oxidizing compound, there is no need for the consumer to undertake a pre-mixing step, just prior to application to hair. The consumer contacts his or her hair with an admixture of hair dye precursors and the nascent oxidizing compound and waits for about 5 minutes to about 60 minutes to elapse during which time the implement provided with the kit is used to align the hair and distribute the precursor solution. Then the consumer contacts his or her hair with the hair color developer mixture, which in this case comprises a persulfate composition and an alkaline buffer system. The consumer then allows about 5 minutes to about 60 minutes to elapse, after which the consumer rinses the hair.

A dual package that can be employed in the products and kits of the present invention is disclosed in U.S. Pat. No. 6,082,588 to Markey et al, which is hereby incorporated by reference.

A variety of alternative implements can optionally be provided with the kit as described above under aligning means: a simple disposable comb or brush, a sponge or towellete or a combination tool. An example of a combination tool is a comb on whose handle is secured a sponge like absorbent sheet overlapping the teeth of the comb.

Desired change in hair color by the method of the invention is described by the mathematical formula described above. Desired change in hair color can be achieved in a number of other ways. In the first instance, the consumer can initially compare his or her hair color with desired hair color or the hair color of a sample tress. Hair dyeing by the method of the invention can be repeated until his or her hair color matches the desired hair color.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of coloring and lightening hair to provide more vibrant, natural and long-lasting color with reduced damage comprising carrying out the following sequential steps:
   (a) contacting said hair with a substantially inactive mixture of oxidative hair dye precursors wherein the rate of oxidation of hair dye precursors/rate of diffusion of hair dye precursors is less than about 1;
   (b) allowing said mixture to remain in said hair for a period of about 5 minutes to about 60 minutes;
   (c) contacting said hair with an aqueous developer composition comprising a mixture of a persulfate salt selected from the group consisting of sodium persulfate, potassium persulfate, ammonium persulfate and mixtures thereof, a peroxide, and a basifying compound, wherein the weight ratio of persulfate salt to peroxide is in the range from about 1 to about 4;
   (d) allowing the composition in step (c) to remain on said hair for a period of about 30 seconds to about 60 minutes.

2. The method according to claim 1, wherein the oxidative hair dye precursor comprises a primary intermediate and optionally a coupler.

3. The method according to claim 2, wherein said primary intermediate and optional coupler are selected from the group consisting of m-aminophenol; 3-methyl-p-aminophenol; 2,3-dimethyl-p-aminophenol; p-phenylene diamine; p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis (4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene- 3-sulfonic acid; thymol(2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole;bis (2,4- diaminophenoxy)-1,3-propane; 1-hydroxyethyl-2,4-diaminobenzene; 2-amino-4-hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 2-dimethylamino-5-aminopyridine; 2,4,5,6-tetraaminopyrimidine; 4,5-diamino-1-methylpyrazole; 4,5-diamino-1-hydroxymethylpyrazole, 4,5-diamino-1-hydroxyethylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 3-amino-5-hydroxy-2,6-dimethoxypyridme; 2-bromo-4, 5-methylenedioxyphenol; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol; 4-hydroxy-2,5,6-triaminopyrimidine, and mixtures thereof.

4. The method according to claim 2, wherein said primary intermediate has a pKa in the range of from about 3 to about 10 and is selected from the group consisting of the neutral or salt forms of para-phenylenediamine, derivatized para-phenylenediamines, para-aminophenol, substituted para aminophenols, 4,5-diaminopyrazole, substituted 4,5-diaminopyrazole, polyamino-pyrimidine, hydroxy-polyaminopyrimidine, and other substituted polyaminopyrimidine and mixtures thereof.

5. The method according to claim 2 wherein the primary intermediate and the optional coupler is each present at a level of from about 0.1 Wt % to about 10 Wt % based on the total weight of the oxidative hair dye precursor mixture and the weight ratio of the primary intermediate to the coupler is in the range of from about 100: to about 1:100.

6. The method according to claim 1, wherein the pH of the mixture of oxidative hair dye precursors is selected such that less than 50% of the molecules comprising the oxidative hair dye precursors are in their anionic form when they first contact the hair before the developer composition is applied.

7. The method according to claim 1, wherein the pH of the mixture of oxidative hair dye precursors is selected such at least 50% of the molecules comprising the oxidative hair dye precursors are in their nonionic forms when they first contact the hair before the developer composition is applied.

8. The method according to claim 1 wherein the aqueous developer is formed by mixing an aqueous solution comprising the peroxide with a solid composition in powder form comprising the persulfate salt.

9. The method according to claim 1 wherein the peroxide of the aqueous developer composition is selected from the group consisting of hydrogen peroxide, urea peroxide, melamine peroxide, sodium perborate, sodium percarbonate and mixtures thereof.

10. The method according to claim 1 further comprising applying to the hair an aligning and distributing means after the hair has been contacted with the oxidative hair dye precursor mixture but before the hair is contacted with the aqueous developer composition.

11. The method according to claim 10 wherein the aligning and distributing means is selected from the group consisting of a comb, a brush, a pick, an elongated element coupled in an open/close relationship, a towelette, a cloth, a sponge and a combination of these implements.

12. A kit for providing more vibrant, natural and long-lasting color to hair which comprises:
(a) a hair colorant composition comprising oxidative hair dye precursors in a container,
(b) a composition comprising a peroxide in a container,
(c) a composition comprising a persulfate salt in a container, said persulfate salt selected from the group consisting of sodium persulfate, potassium persulfate, ammonium persulfate and mixtures thereof,
(d) an alkaline composition used to activate the peroxide/persulfate
(e) written instructions that direct that the hair colorant composition is first applied to the hair as a substantially inactive mixture for about 5 minutes to about 60 minutes before a hair color developer composition, created by mixing the peroxide composition, the persulfate salt composition and the alkaline composition, is applied to the hair, wherein the oxidative hair dye precursors of the hair colorant composition satisfies the condition that the rate of oxidation of hair dye precursors/rate of diffusion of hair dye precursors <1 when the hair colorant composition is applied to the hair before the hair is contacted with the hair color developer composition.

13. The kit according to claim 12 further comprising a hair an aligning and distributing means that contains at least one comb element or at least one brush element.

14. The kit according to claim 13, wherein the aligning and distributing means is selected from the group consisting of a comb, a brush, a pick, an elongated element coupled in an open/close relationship, a towelette, a cloth, a sponge and a combination of these implements.

15. The kit according to claim 12 further comprising conditioning agents, color sealants, damage control agents, hair benefit agents, perfumes, moisturizers and mixtures thereof, either packaged separately or as part of the oxidative hair dye precursor, peroxide or persulfate compositions.

16. The kit according to claim 12 wherein the persulfate salt is a solid in powder form.

* * * * *